(12) United States Patent
Morales et al.

(10) Patent No.: US 11,172,951 B2
(45) Date of Patent: Nov. 16, 2021

(54) SURGICAL INSTRUMENT WITH LOCKABLE LEGS

(71) Applicant: Aesculap AG, Tuttlingen (DE)

(72) Inventors: Pedro Morales, Tuttlingen (DE); Karsten Noll, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 221 days.

(21) Appl. No.: 16/482,142

(22) PCT Filed: Feb. 1, 2018

(86) PCT No.: PCT/EP2018/052518
§ 371 (c)(1),
(2) Date: Jul. 30, 2019

(87) PCT Pub. No.: WO2018/141848
PCT Pub. Date: Aug. 9, 2018

(65) Prior Publication Data
US 2019/0343540 A1  Nov. 14, 2019

(30) Foreign Application Priority Data
Feb. 2, 2017 (DE) .......................... 102017102027.6

(51) Int. Cl.
*A61B 17/28* (2006.01)
*A61B 17/062* (2006.01)
*A61B 17/00* (2006.01)

(52) U.S. Cl.
CPC ........ *A61B 17/2833* (2013.01); *A61B 17/062* (2013.01); *A61B 17/282* (2013.01);
(Continued)

(58) Field of Classification Search
CPC . A61B 17/285; A61B 17/122; A61B 17/2946; A61B 17/08; A61B 17/30;
(Continued)

(56) References Cited

U.S. PATENT DOCUMENTS

| 1,327,577 A | 1/1920 | Turner |
| 3,176,689 A | 4/1965 | Yahr |

(Continued)

FOREIGN PATENT DOCUMENTS

| DE | 8702813 U1 | 5/1987 |
| DE | 10392131 T5 | 10/2004 |

(Continued)

OTHER PUBLICATIONS

German Examination Report for German Application No. 10 2017 102 027.6, with English translation, dated Nov. 22, 2017—15 pages.

(Continued)

*Primary Examiner* — Kathleen S Holwerda
*Assistant Examiner* — Lauren Dubose (57) ABSTRACT

A medical or surgical instrument, preferably of the pincers, scissors and/or forceps design, includes at least two legs pivoted relative to each other in a pivoting plane and lockable in at least one pivoting direction and in at least one pivoting position. The legs include locking portions adapted to be brought into locking engagement with each other, with the locking portions offset against each other normal to the pivoting plane by such offset that, when the legs are pivoted in the pivoting plane, the locking portions laterally pass each other in the pivoting plane without getting into locking engagement with each other. The medical or surgical instrument is configured in such way that the locking engagement of the locking portions is implemented only by applying a transverse force normal to the pivoting plane to at least one of the legs while cancelling the lateral offset.

20 Claims, 5 Drawing Sheets

(52) U.S. Cl.
CPC ............... *A61B 2017/00862* (2013.01); *A61B 2017/2837* (2013.01)

(58) Field of Classification Search
CPC ... A61B 17/44; A61B 17/282; A61B 17/2841; A61B 17/062; A61B 17/28; A61B 17/29; A61B 17/2833; A61B 2017/1225; A61B 2017/00407; A61B 2017/00353; A61B 2017/00862; A61B 2017/2837; B25B 9/02
USPC ......................................................... 606/208
See application file for complete search history.

(56) References Cited

U.S. PATENT DOCUMENTS

| | | | | |
|---|---|---|---|---|
| 4,475,544 | A | * | 10/1984 | Reis ................... A61B 17/8866 606/151 |
| 4,722,339 | A | | 2/1988 | Dreier et al. |
| 2004/0106947 | A1 | | 6/2004 | Propp et al. |
| 2008/0287985 | A1 | * | 11/2008 | Patterson ............. A61B 17/282 606/208 |
| 2014/0155700 | A1 | | 6/2014 | Terry et al. |
| 2018/0103995 | A1 | * | 4/2018 | Ding .................. A61B 18/1442 |

FOREIGN PATENT DOCUMENTS

| | | | |
|---|---|---|---|
| EP | 0218544 | A1 | 4/1987 |
| FR | 2927247 | * | 8/2009 |
| FR | 2927247 | A1 | 8/2009 |
| WO | 2014097494 | A1 | 6/2014 |

OTHER PUBLICATIONS

International Search Report and Written Opinion for International Application No. PCT/EP2018/052518, dated Apr. 24, 2018—10 pages.

* cited by examiner

SURGICAL INSTRUMENT WITH LOCKABLE LEGS

CROSS REFERENCE TO RELATED APPLICATION(S)

This application is the United States national phase entry of International Application No. PCT/EP2018/052518, filed Feb. 1, 2018, which claims the benefit of priority of German Application No. 10 2017 102 027.6, filed Feb. 2, 2017. The contents of International Application No. PCT/EP2018/052518 and German Application No. 10 2017 102 027.6 are incorporated by reference herein in their entireties.

FIELD

The present invention relates to a medical or surgical instrument, preferably of the pincers, scissors and/or forceps type, such as a surgical needle holder or a (surgical) forceps, comprising at least two legs adapted to be pivoted toward each other in a pivoting plane and lockable in at least one pivoting direction and in at least one pivoting position, which legs include locking portions adapted to be brought into locking engagement with each other.

BACKGROUND

Medical or surgical instruments frequently require the instrument parts thereof, in the form of pivoting legs, to be locked relative to each other so as to equally (temporarily) fix a distal effective portion having e.g. branches, cutting blades, forceps tips etc.

As an example of a medical/surgical instrument and for illustrating the current problems, hereinafter a surgical needle holder is exemplified.

Surgical needle holders are a medical working equipment by which the needle is held and guided during surgical or medical suturing. During surgical suturing, tissue is joined together by means of needle and thread so as to place wound layers next to each other in a tension-free manner and thus to effectuate wound healing. During a suturing process, needles of most various designs have to be safely handled by the needle holder in different applications.

For example, a (surgeon's/operating surgeon's/physician's) assistant can clamp a needle in a needle holder and lock the needle holder in place with adjustable clamping force so as to subsequently hand said needle holder in a targeted/directed and safe manner to the operating surgeon.

During suturing, the operating surgeon seizes the needle holder by the strong hand, with the thumb and the ring finger reaching through holes of the actuating grips/actuating portions. The middle finger contacts the leg/scissors neck and the index finger contacts the (scissors) joint. The rear third of the needle is clamped at the proximal end of the two gripping jaws of the needle holder. The operating surgeon stitches, by a supination movement, the epidermis and cutis from the top to the bottom and stitches out within the wound or beneath the wound. The stitch is finally contracted by an instrument knot.

By way of the afore-described configuration of a suture with the different suture forms it is evident that for a suture the operating surgeon has to repeatedly grasp and release the needle. Moreover, knotting requires to open and close the clamping portions/gripping jaws.

Apart from the surgical needle holder, in medicine/surgery also medical/surgical forceps as an example of medical/surgical instruments are utilized. They serve especially for grasping objects and tissue parts and for safe fixation thereof.

From DE 103 92 131 T5 a surgical instrument, especially a needle holder, is known comprising a first longitudinal member having a grip end, a working tip and a box joint member between the grip end and the working tip and comprising a second longitudinal member having a grip end, a working tip and a box joint member between the grip end and the working tip, wherein the first box joint member is defined by a slit having generally flat parallel sides for receiving the second box joint therein and wherein the second box joint member takes a cross-sectional shape adapted to the flat parallel sides of the slit and in general at both sides of the box joint member is continuous in width with the grip end and the working tip, and wherein a joint pin extends through the parallel sides of the slit and through the second box joint member and articulates the first longitudinal part to the second longitudinal part. The grip ends comprise interacting closing mechanisms that are arranged in the vicinity of the circular grips and can be closed together so as to efficiently close the remote tips of the first and second longitudinal parts by latching.

From U.S. Pat. No. 1,327,577 A, likewise a surgical needle holder is known which comprises a pair of pivoted gripping jaws having grooves in their gripping surface. The two jaws are retained in a clamping position by a spring catch.

In said surgical instruments that are in the form of needle holders, according to the current state of the art respective locking portions having a geometric toothing are provided at two opposite legs which, upon pivoting in the pivoting plane of the two legs against each other, enter into locking engagement with each other during a closing movement and thus, during closing of the medical/surgical instrument, (automatically) cause a lock/latch.

During the afore-described suturing operation, an operating surgeon has to repeatedly open and close the gripping jaws so as to grasp and release a needle and guide the same through the skin and, resp., the wound area according to a specific pattern. In order to prevent the gripping jaws from locking in place, the operating surgeon has to force the two legs apart perpendicularly to the pivoting plane with great effort and has to maintain the same for a quite long time at said position, which may entail aching pressure sores (pressure on the nerves) up to numbness and loss of sensation lasting several days at the operating surgeon's actuating hand and, resp., fingers.

This configuration equally causes a restriction in the operation process inter alia by an increased fatigue of the operating surgeon. Moreover, the tactile sensation during guiding of the needle and the thread as well as the use thereof is strongly limited by the effort required. Furthermore, little user friendliness, suboptimal ergonomics and further restrictions of the user are resulting. In the case of surgical forceps without any lock or forceps with automatic lock, likewise increased fatigue of the operating surgeon owing to the effort required as well as a loss of the tactile sensation will occur.

SUMMARY

In view of these current problems, it is the object of the present invention to eliminate or at least reduce the drawbacks from prior art and in particular to provide a generic medical and/or surgical instrument, such as a medical/surgical needle holder, medical/surgical forceps, medical/ surgical pincers and/or medical/surgical scissors, which (for example when handed to the surgeon by an assistant) includes automatic holding in a closed state or a clamping position of holding even without any manual action in the locking engagement (with the lock/latch being activated/in the locked state) and during use by the physician/surgeon in particular admits guiding and holding of an object with high tactile sensation, when the locking engagement is missing (with deactivated lock/in the non-locked state). By controlled efforts and correspondingly minimum fatigue an improvement of the treatment/operation process is intended to be achieved.

Consequently, according to the invention it is provided that in a medical and/or surgical instrument the locking portions are offset against each other normal to the pivoting plane with such offset that, when the legs are pivoted in the pivoting plane, the locking portions laterally pass each other (at the sides) without entering into locking engagement with each other, and the medical or surgical instrument is designed such that the locking engagement of the locking portions is only implemented by applying a transverse force normal to the pivoting plane to at least one of the legs while cancelling the lateral offset. Offset in this case means the lateral distance/the distance normal to the pivoting plane/the lateral space that has to be overcome so as bring the two locking portions into locking engagement with each other.

It is thus a basic idea of the invention to provide an operating surgeon for his/her handling with a medical/surgical instrument, such as needle holder or forceps, which can be repeatedly opened and closed during use without locking the legs in place (deactivated latch). More exactly speaking, pivoting of the legs toward each other in the pivoting plane is admitted for realizing e.g. handling of a needle with high tactile sensation without having to force the latch apart with great effort in order to hold it deactivated in this way for a quite long time.

For example, when the assistant hands a needle to the surgeon or when the surgeon grasps a tissue portion, an object can be automatically gripped/held without any manual action by locking the two locking portions. For locking a transverse force is applied to at least one leg normal to the pivoting plane, preferably in an opened state of the instrument, which causes the existing offset of the two locking portions relative to each other to be cancelled.

In this way, during a subsequent pivoting movement in the closing direction, the locking portion of the one leg engages in the locking portion of the other leg and is in locking engagement so that the at least two legs pivoted toward each other in a pivoting plane are locked in at least one pivoting direction and in at least one pivoting position. In this manner, for example a needle can be safely fixed and can be provided, when preparing an operation, in a locked state on a work table for the surgical case in order to be handed to the surgeon by the assistant in a safely gripping state during the later process. The risk of the object to be gripped falling out of the gripping range of the needle holder or of the forceps is minimized.

In other words, a medical or surgical instrument, preferably of the pincers, scissors and/or forceps design, is provided including two instrument parts (legs) supported pivotally relative to each other each consisting of an active portion (gripping portions/clamping-/fixing branches, cutting blades, forceps tips etc.) and a handle portion (actuating portion) connected thereto in the longitudinal instrument direction at which portions effectively engaging projections (locking portions) projecting in the pivoting/closing direction of the instrument parts are formed, preferably in the area of the handle portions, which are arranged and/or oriented in such way that during a closing movement they run/slide past each other, preferably non-contacting. The effectively engaging projections and/or the instrument parts, in particular in the area of the handle portions, and/or the bearing (joint) pivotally coupling the two instrument parts have a predetermined elasticity/flexibility at least in the direction transversely/perpendicularly to the closing direction/closing plane/pivoting plane of the instrument which is dimensioned so that the two effectively engaging projections are resiliently (manually) movable toward each other in the transverse direction relative to the closing direction so as to effectively engage each other (stop/holding engagement/locking engagement) and to (temporarily) fix the instrument in the current closing position. Preferably, said effective engagement is releasable, in particular by applying a transverse counter-force to the instrument parts.

Preferably, the locking engagement of the medical/surgical instrument is implemented positively (by form-closure) and/or frictionally and/or adhesively. The legs may be locked by designing the locking engagement and, resp., the locking portions by means of positive closure (form closure/form fit) or frictional closure or adhesive closure or else by a combination of said three variants.

Preferably, in the medical/surgical instrument such as the needle holder or the forceps at least one leg as a whole or at least a portion hereof may be formed elastically in a direction normal to the pivoting plane. Said elastic/flexible design allows to achieve an elastic deflection of the legs toward each other normal to the pivoting plane and an accompanying reduction of the offset, when a transverse force is easily applied by the operating surgeon, in the case of an elastic material of the leg even without the need of further components such as joints or springs. When the transverse force is omitted in the non-locked state, the leg again adopts its original shape and position and the two locking portions of the two legs again pass each other without entering into locking engagement with each other. In particular, due to an elastic design in parallel to the pivoting plane of at least one portion of a leg, a gripping force of the medical/surgical instrument can be obtained. In particular, metals or, resp., alloys, especially preferred stainless steel, are used as elastic materials for the legs.

For compensating elastic material properties, the clamping area of the medical/surgical instrument may include an insert made from wear-resistant material, in particular hard metal, so as to grip e.g. objects such as needles with minimum wear.

In order to minimize possible friction and wear when pivoting the legs in the pivoting plane, the two locking portions may be offset against each other normal to the pivoting plane by such offset that during pivoting of the legs in the pivoting plane they exhibit a gap therebetween so that the locking portions are passing each other without contacting each other. Other than in the case of sliding past each other, a specific form of the locking portions of the legs laterally passing each other, the locking portions pass each other at a certain distance from each other.

Advantageously, the two (corresponding) locking portions may be arranged at the sides of the legs facing each other, and may preferably be formed integrally with the leg. Such arrangement allows the locking portions to be easily brought into locking engagement with each other in the case of specific locking in place. For the locking portions both an integral design with the corresponding leg and a modular/multi-part design realized by e.g. a clip system are considered. In the case of an integral design, the leg can be formed and manufactured together with the locking portion in a production process of the legs. In this way, an integral construction with firm hold is achieved without the necessity of any assembly and with facilitated sterilization. By modular design, in particular by a clip system, the medical/surgical instrument such as the needle holder or the forceps can be adapted corresponding to their intended use. Different offsets of the locking portions with correspondingly different transverse forces to be applied are imaginable just as different forms and configurations of the locking portions for different locking engagements and gripping forces.

Each of the legs of the medical/surgical instrument may usefully include at their distal ends a clamping portion/gripping portion/functional portion/branch which can be actuated via actuating portions, proximal in the case of the needle holder, and preferably a joint or mechanism (bearing) arranged therebetween in the needle holder and arranged proximally in the case of the forceps, wherein the first locking portion is arranged relative to the pivoting plane at the first leg opposite to the first actuating portion and the second locking portion is arranged relative to the pivoting plane at the second leg opposite to the second actuating portion. The two corresponding locking portions are preferably arranged in the area of the actuating portions. In the embodiment of the medical/surgical instrument in the form of forceps, the joint may be formed by an elastic proximal area/portion. By arranging the locking portions in the area of the actuating portions, a proper lever arm can be implemented in order to deflect, in particular elastically, the two legs when applying a transverse force to at least one leg and to cancel the offset. The actuating portion of the medical/surgical instrument includes, when viewed from the joint, an appropriate distance along the longitudinal axis of the legs, thus promoting elastic deflection.

Preferably, the locking engagement may be positive and each of the locking portions for this purpose has a locking engagement side with a geometric stop structure, in particular in the form of a toothing including at least one tooth, wherein the locking engagement sides arranged at the legs complementarily relative to the pivoting plane admit further, in particular elastic, pivoting of the legs in the pivoting plane in the case of locking engagement in the one pivoting direction (in particular in the closing pivoting direction) and in the opposite pivoting direction lock the legs in a pivoting position. Stop structures having a toothing are proven configurations for positively bringing two locking portions into locking engagement. In particular, the tooth or, resp., the teeth of such toothing may have a respective undercut so as to form an even better hold/barb. The ramp respectively the structure of the ramp allows the complementarily arranged teeth to slide (past) along each other in one direction in the case of locking engagement. The locking engagement side of the one leg either may be arranged facing the locking engagement side of the other leg or may be arranged facing away therefrom with appropriate offset.

It is recommended that the stop structure of the locking portion includes plural stop planes, in particular plural teeth, wherein an increase in the gripping force can be reached by increasing the number of stop planes, in particular teeth, being in locking engagement. Such stop structures having plural stop planes, in particular plural teeth, have already been used in medical engineering and cause, in particular with elastically forming legs or legs having elastic portions, a gripping force acting on an object to be gripped, such as a needle, to be further increased. For compact tissues or areas that are hard to penetrate such increased gripping force is required to ensure safe holding and guiding. In this way, a stepwise increase in the gripping force can be realized via plural stop planes.

It has turned out that it is advantageous when the locking portion includes a smooth side opposite (when viewed perpendicularly to the pivoting plane) to its locking engagement side, in particular the side configured as stop structure in order to prevent inadvertent locking engagement of the locking portion during pivoting of the legs. The smooth side is rounded in particular circumferentially so as to further improve the smooth sides to slide past each other. When the medical/surgical instrument is normally opened and closed, said smooth sides preferably are facing each other and the legs may be pivoted in the pivoting plane without the locking portions inadvertently entering into locking engagement with each other. Thus, the direction of a transverse force to be applied in this case points from the locking engagement side of the locking portion toward the smooth side of the same locking portion. In the case of a possible transverse force acting on both legs, the transverse forces point in the respective opposite direction.

In order to implement lateral offset of the two locking portions preferably a portion of at least one leg may have an extension with a perpendicular component/part relative to the pivoting plane in the longitudinal direction. In particular preferred, the legs include a bending in the opposite direction toward the proximal side perpendicularly to the pivoting plane away from each other. This causes implementation of a lateral offset of the locking portions normal to the pivoting plane against each other. When in the pivoting plane a corresponding variant of the medical/surgical instrument is viewed from above, a variant might include e.g. a leg extending in parallel to the pivoting plane/extending straightly as well as a leg which extends offset in portions normal to the pivoting plane and, in this way, describes an S shape when viewed from above. In another variant, the medical/surgical instrument could have two legs which describe a bending opposite to the actuating portion normal to the pivoting plane and thus cause an offset of the locking portions to be implemented.

Preferably, the locking portions, in particular at least one possible locking engagement side of the locking portions, may be made from wear-resistant material, or at least the surface of the locking portions, in particular the locking engagement side, may be provided with wear-resistant material. In this way, long durability and service life of the medical/surgical instrument is intended to be ensured.

In particular, the dimension of the locking engagement side of the locking portions may increase in the pivoting plane toward the actuating portion of the respective leg, and/or the locking engagement side of the locking portions may include higher offset against each other normal to the pivoting plane toward the actuating portion.

Hence it is of advantage when at least one of the two locking portions, alternatively or additionally to the form closure of the locking portions, includes a non-positive friction lining so as to lock the two legs relative to each other and to obtain a locking engagement of the locking portions. Instead of or additionally to the form closure, in this variant for locking in the case of locking engagement use is made of the pressure of the two locking portions normal to the pivoting plane against each other with perpendicular force component on the surface of the locking engagement side of the locking portions. At least one of the two locking portions includes a friction lining on the locking engagement side and preferably both locking portions include a friction lining. The friction of the friction lining causes the legs to lock in the case of locking engagement. Alternatively or additionally to the force closure (in particular friction lining) as well as alternatively or additionally to the form closure (in particular stop structure), at least one locking portion may include an adhesive lining for an adhesive connection and the locking engagement of the locking portions. The adhesive lining in particular is a releasable adhesive lining in order to be able to release the legs again after locking/a locking engagement. In particular preferred, only one locking portion includes the adhesive lining, whereas the other locking portion includes an (appropriate) complementary surface for safely and detachably connecting the adhesive lining of the one locking portion to the complementary surface of the other locking portion.

Preferably, when viewed in the direction normal to the pivoting plane, the sides of the locking engagements of at least two locking portions are facing each other (for example as the adhesive lining or a Velcro fastener is included in the locking portion), wherein in a locking engagement the locking portions are subjected to tension (pull), or are facing away (remote) from each other wherein in a locking engagement the locking portions are subjected to pressure (push) and are in particular formed substantially in parallel to each other.

In other words, a medical/surgical instrument, such as needle holder or forceps, preferably includes a pivoting position detent consisting of two locking portions/halves/parts/projections, with a respective side of a locking portion/a half/a part/a projection thereof in particular including a toothing and the other side/opposite side (of the toothing) in particular being smooth. Said locking portions/halves/parts/projections are located at the inner sides of the legs/the sides of the legs facing each other. The smooth sides (of the locking portions) are pointing either toward each other or away from each other, while the toothing points/projects in the lateral direction/perpendicularly to the pivoting plane. In order to prevent friction, a gap is provided between the locking portions. The pivoting position detent/locking is not active during opening and closing of the jaw part/the clamping portions and, resp., during pivoting of the legs against each other. For activating the pivoting position detent/locking, the legs have to be forced apart in a targeted manner and, resp., a transverse force has to be applied to the legs normal to the pivoting plane.

The functional element/the pivoting position detent thus consists of two parts/locking portions which together enable a detent function/locking (in locking engagement). Due to an offset of the two parts/locking portions, the detent function/locking is deactivated during normal opening and closing (pivoting of the legs in the pivoting plane)/does not enter into locking engagement during pivoting. For activating the detent function, a (targeted) transverse force has to be applied (to the legs normal to the pivoting plane). The medical or surgical instrument thus has a (passive) pivoting position detent/locking which only engages for intended activation/may enter into locking engagement and grips the content in the claw area/gripping portion of the medical or surgical instrument in a self-locking manner (keeping automatically closed or maintaining the gripping position even without any manual action in the locking engagement/in the locked state). Otherwise, when applying the medical or surgical instrument, the user has the best possible sensation and impact as well as reduced impacts on fatigue and aching.

At this point, in the following some important definitions shall be discussed. The opened state of the medical/surgical instrument is the state in which the clamping portions/functional portions are opened. Accordingly, the closed state is the state in which the clamping portions/functional portions are closed.

The opening direction is the direction in which the medical/surgical instrument is opened by pivoting the legs. Accordingly, the closing direction is the direction in which the medical/surgical instrument is closed by pivoting the legs.

In the case of locking engagement, a stop position is a position in which the locking portions are in locking engagement with each other.

The locked state is the state in which the locking portions are in locking engagement and, resp., the legs of the medical/surgical instrument are locked.

The (normal) opening and closing of the medical/surgical instrument denotes pivoting of the legs against each other in the pivoting plane, e.g. similarly to a pair of scissors, without any transverse force being applied to the legs normal to the pivoting plane or any locked state being brought about.

BRIEF DESCRIPTION OF THE DRAWING FIGURES

The present invention hereinafter shall be illustrated in detail by way of preferred embodiment with reference to the accompanying Figures.

DETAILED DESCRIPTION

The Figures are schematic and are merely intended to serve for the comprehension of the invention. Like elements are provided with like reference numeral. The features of the various embodiments may be exchanged.

Figure 1:
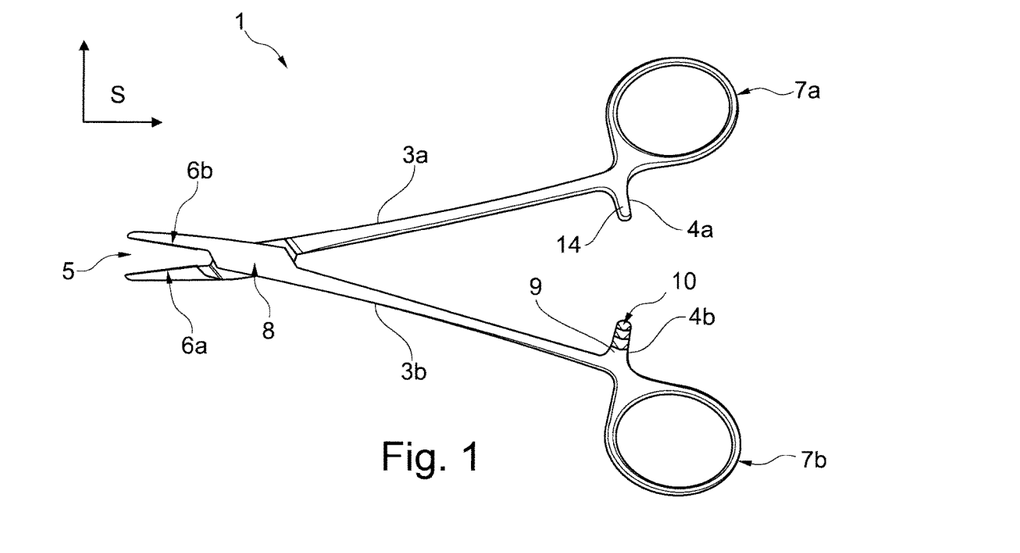
FIG. 1 shows a side view of a first preferred embodiment of a surgical instrument in the form of a needle holder in an opened state, with the distal gripping portions being open and the locking portions not being in locking engagement with each other.

FIG. 1 illustrates a medical or surgical instrument according to the invention of a first preferred embodiment in the form of Hegar's (surgical) needle holder 1. The needle holder 1 includes a first leg 3a and a second leg 3b which are pivoted relative to each other in a first pivoting plane S, similarly to scissors or fixation forceps. The first leg 3a includes a proximally arranged, tongue-shaped first locking portion 4a on the inner side and, resp., on the side facing the second leg 3b. Said first locking portion 4a extends in the direction of the second leg 3b. The second leg 3b, on the other hand, has a proximally arranged second locking portion 4b which is equally tongue-shaped and projects toward the first leg 3a. The second locking portion 4b is formed identically with the first locking portion 4a but is arranged complementarily to the first portion 4a on the second leg 3b. Complementary in this context means that the second locking portion 4b is rotated vis-à-vis the first locking portion 4a substantially by 180° about the longitudinal axis of the second leg 3b.

The two halves of the locking/detent/interlock and, resp., the two locking portions 4a, 4b are arranged on the opposite/facing sides of the legs 3a, 3b and are formed integrally with the corresponding legs 3a, 3b. The second leg 3b takes an S shape relative to the pivoting plane S (see FIG. 10), i.e. in the longitudinal direction of the second leg 3b an extension with a perpendicular component relative to the pivoting plane S so as to implement an offset/distance V (see FIG. 2) between the two locking portions 4a, 4b. The two locking portions 4a, 4b in this way are laterally offset relative to each other normal to the pivoting plane S with such offset V that during normal opening and closing of the legs 3a, 3b they laterally pass each other without entering into locking engagement.

At the distal end 5 of the needle holder 1 a clamping area/gripping area/jaw area/branch including a first gripping portion/a first gripping jaw 6a of the associated first leg 3a as well as a corresponding second gripping portion 6b is formed on the second leg 3b. Each of the two gripping portions 6a and 6b has an insert with a wafer-type corrugated surface structure made from wear-resistant hard material on their sides facing each other so as to obtain as little wear as possible during receiving, holder and guiding a needle. Since the needle holder 1 is not only used for stitching and holding but also for knotting, the gripping portions 6a, 6b as well as the legs 3a, 3b are largely rounded to the outside as well as designed to be smooth and non-meshing.

The proximal end of the first leg 3a includes a first actuating portion 7a in the form of an oval-shaped handle with a hole which handle is formed integrally with the leg 3a. The first handle 7a is opposed, when viewed in the pivoting plane S, to the first locking portion 4a at the first leg 3a. Correspondingly, at the second leg 3b a second handle 7b is formed which is opposed, when viewed in the pivoting plane S, to the second locking portion 4b at the second leg 3b. Both the handles 7a, 7b and the transitions toward the leg are rounded and smooth. The size and shape of the holes of the handles 7a, 7b are shaped so that each of them is adapted to receive one finger. Of course, a further improvement, in particular regarding ergonomics, is possible by varying the shape of the handles 7a, 7b. For example, a handle 7b could receive two fingers instead of only one, or different geometric changes of shape could be made to ensure optimum contact of the fingers and the hand with the handles 7a, 7b.

Via a joint 8, which in this embodiment is a box joint, the gripping portions 6a, 6b may be closed and opened by actuating and, resp., guiding the handles 7a, 7b and pivoting the legs 3a, 3b. The second leg 3b is slit in the area of the joint 8, having flat parallel sides, and is prepared for receiving a joint portion of the first leg 3a which at this point is slim and substantially rectangular. A predefined pressure of the parallel sides of the second leg 3b vis-à-vis the parallel sides of the joint portion of the first leg 3a effectuates a self-gripping force/self-gripping of the pivoting movement of the legs 3a, 3b relative to each other in the pivoting plane S. Opening and closing of the needle holder 1 and, resp., pivoting of the legs 3a, 3b relative to each other can only be effectuated and inadvertent pivoting can only be prevented actively by the user.

An operating surgeon grasps a needle holder 1 according to the invention by the usual thumb-and-ring finger grip. For locking the two legs 3a, 3b by means of the locking engagement, the operating surgeon applies an opposed transverse force normal to the pivoting plane S to the two legs 3a, 3b via the two handles 7a, 7b, when the gripping portions 6a, 6b are opened. Hence the operating surgeon forces the two handles 7a, 7b toward each other perpendicularly/normal to the pivoting plane S. In this embodiment, the legs 3a, 3b are made from an alloy having a predefined elasticity so that the transverse force causes lateral deflection of the legs 3a, 3b normal to the pivoting plane S toward each other. The existing offset V of the two locking portions 4a, 4b against each other is cancelled in this way and, during a following closing movement of the legs 3a, 3b by the operating surgeon, the two locking portions 4a, 4b enter into locking engagement with each other while maintaining the transverse force. Now the operating surgeon stops applying the transverse force.

In order to release the locking engagement of the two locking portions 4a, 4b again, a transverse force is applied once again, as common with known needle holders, normal to the pivoting plane S to the handles 7a, 7b and the locking portions 4a, 4b are forced apart so as to disengage the locking portions 4a, 4b. The two legs 3a, 3b are pivoted against each other while maintaining the transverse force and the needle holder 1 is opened. After the transverse force is stopped by the operating surgeon in the opened state of the needle holder 1, the latter subsequently can be opened and closed again, viz. the legs 3a, 3b can be pivoted toward each other in the pivoting plane S without the locking portions 4a, 4b getting into locking engagement with each other.

The handles 7a, 7b as well as the locking portions 4a, 4b are gold-coated for in particular proper handling, an anti-bacterial effect, reduced wear and optical marking.

Figure 2:
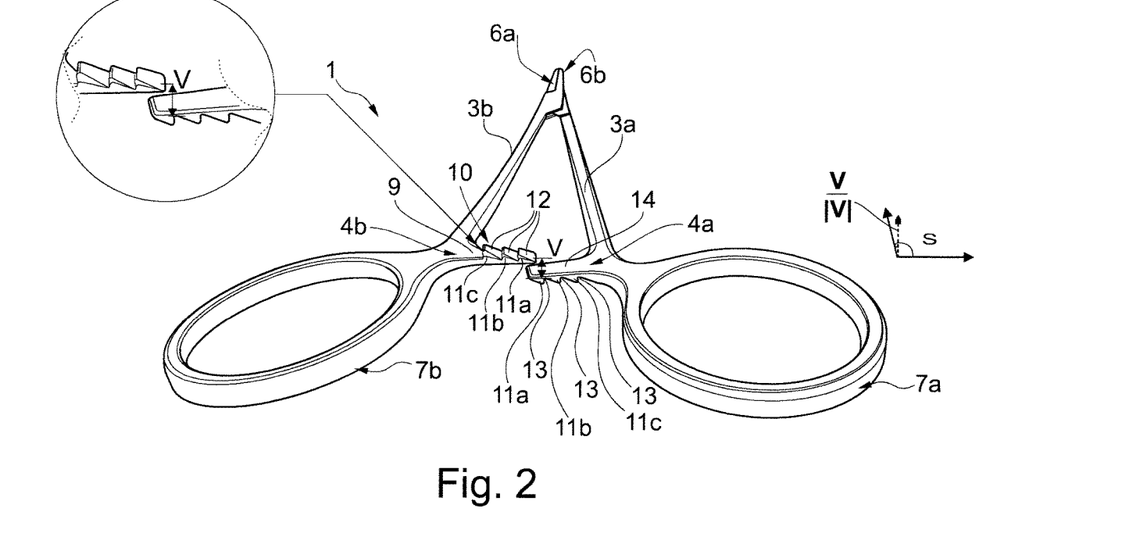
FIG. 2 shows a rear view (proximal perspective) of the first embodiment of the needle holder in a closed state, with the distal gripping portions being closed and the locking portions not being in locking engagement with each other.

FIG. 2 illustrates the first preferred embodiment of the needle holder 1 from the proximal perspective, wherein the clamping portions 6a, 6b are closed and the locking portions 4a, 4b are not in locking engagement. Both the first locking portion 4a and the second locking portion 4b have a locking engagement side 9 with a stop structure 10. Each stop structure 10 includes three teeth/notches 11a, 11b, 11c with ramps/sliding surfaces 12 and with barbs 13. The ramp/ramp structure 12 enables a closing movement of the needle holder 1 by the teeth 11a, 11b, 11c of the opposite complementary stop structure 10 sliding past each other, when the locking portions 4a, 4b are in locking engagement. The barbs/undercuts 13 of the teeth 11a, 11b, 11c, on the other hand, in the case of locking engagement prevent the needle holder 1 from opening, thus allowing the gripping portions 6a, 6b to grip e.g. a needle automatically without any manual impact.

The locking engagement side 9 of the locking portions 4a, 4b is opposed, when viewed perpendicularly to the pivoting plane S, to a smooth side 14 having rounded edges. The two smooth sides 14 of the two locking portions 4a, 4b without any locking engagement point toward each other and include a gap therebetween. The smooth sides 14 prevent the two locking portions 4a, 4b from getting inadvertently caught during (normal) opening and closing/pivoting of the legs 3a, 3b against each other.

Figure 3:
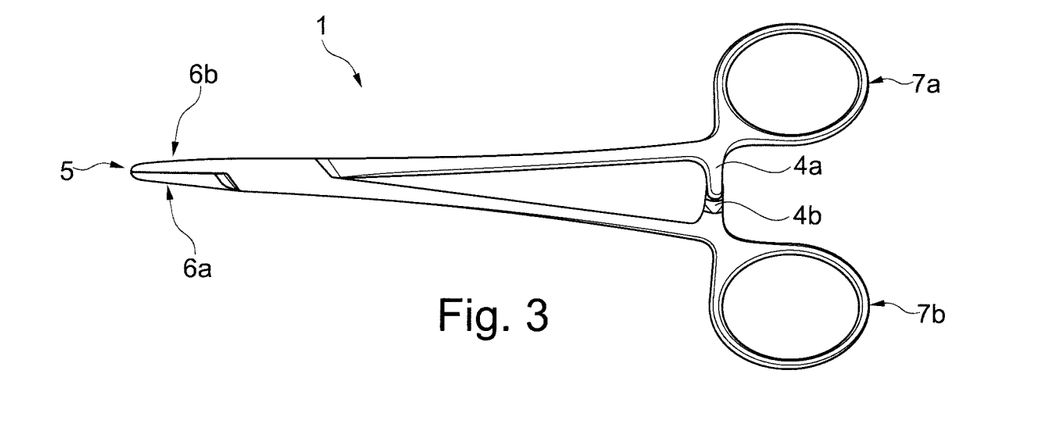
FIG. 3 shows a side view of the first embodiment of the needle holder, wherein the distal gripping portions are closed and the opposite locking portions are in locking engagement in a first snap-fit position.

FIG. 3 shows the needle holder 1 from FIGS. 1 and 2 with closed gripping portions 6a, 6b as well as locking portions 4a, 4b which are in positive locking engagement at a first stop position. The first stop position is defined in such way that the respective first teeth 11a of the locking portions 4a, 4b are in locking engagement and the second and third teeth 11b, 11c are not in locking engagement. More exactly speaking, the barb 13 of the first tooth 11a of the first locking portion 4a is in positive locking engagement with the barb 13 of the complementarily arranged first tooth 11a of the second locking portion 4b. For the locking engagement, the two legs 3a, 3b were appropriately deflected before perpendicularly to the pivoting plane S and were forced against each other so as to cancel the offset V. The two legs 3a, 3b were compressed against their elastic force and, resp., were pivoted further in the closing direction against each other after closing the gripping portions 6a, 6b (see FIG. 1) in order to reach the first stop position of the locking portions 4a, 4b.

The legs 3a, 3b are under tension, due to the elastic deformation, so that also the two barbs 13 of the first teeth 11a of the locking portions 4a, 4b being in locking engagement are under t) tension against each other in the opening direction and are forced against each other. In this way, the legs 3a, 3b of the needle holder 1 are locked at a first pivoting position in the opening direction.

Figure 4:
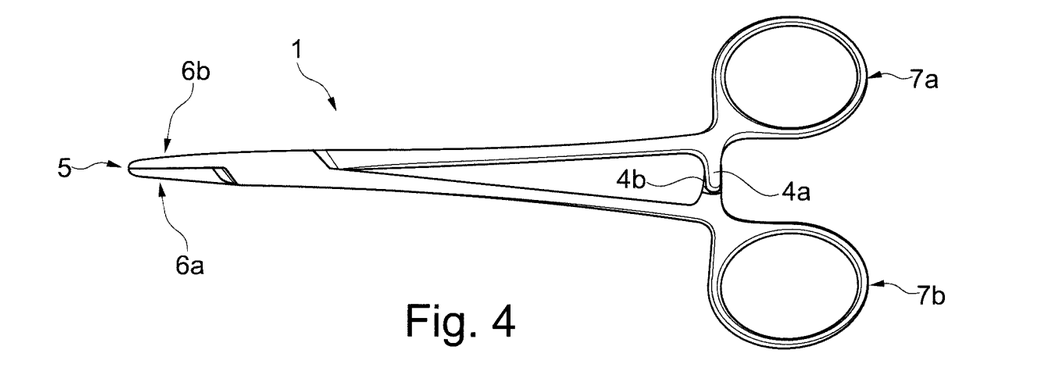
FIG. 4 shows a side view of the first embodiment of the needle holder, wherein the distal gripping portions are closed and the opposite locking portions are in locking engagement in a second snap-fit position.

In FIG. 4, the needle holder 1 from FIG. 1 to FIG. 3 is illustrated in a second stop position at a second pivoting position. Due to the ramp structure 12 of the stop structure 10, in a first stop position of the needle holder 1 the operating surgeon merely has to apply a pressure in parallel to the pivoting plane S in the closing direction to the handles 7a, 7b. The two handles 7a, 7b are forced against each other, as in the case of scissors, and the complementarily arranged (first and second) teeth 11a, 11b of the two locking portions 4a, 4b slide over the ramp structure 12 against each other and admit movement in the closing direction. After a closing movement, the first and second teeth 11a and 11b will latch/get caught due to the internal stress of the legs 3a, 3b in a second stop position and the two complementarily arranged teeth 11a and 11b of the locking portions 4a, 4b are in locking engagement with each other. A resulting gripping force of the two gripping portions 6a, 6b is higher, due to the higher elastic deformation of the two legs 3a, 3b in the second stop position, than in the first stop position.

Figure 5:
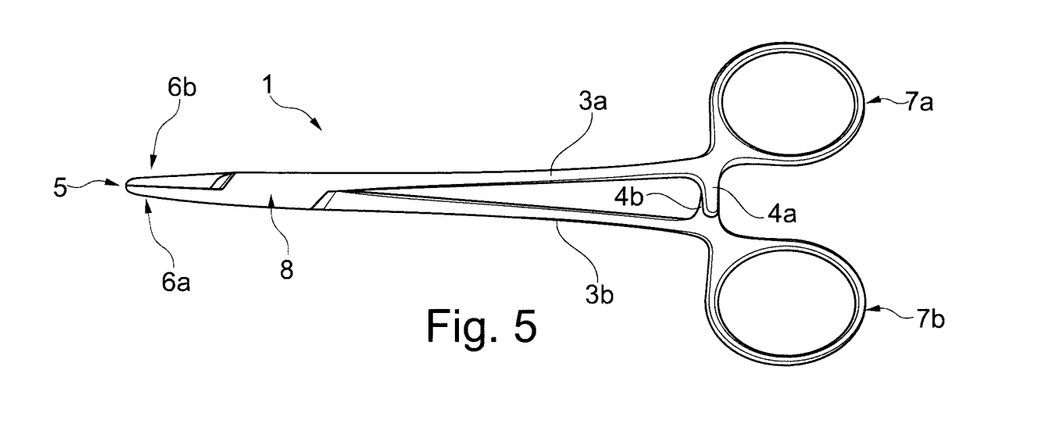
FIG. 5 shows a side view of a second preferred embodiment of the surgical instrument in the form of a needle holder, wherein the distal gripping portions are closed and the opposite locking portions are in locking engagement in a third snap-fit position.

FIG. 5 illustrates a medical or surgical instrument 1 of another preferred embodiment in the form of a (further) needle holder. The needle holder 1 of the second embodiment includes the same technical features as the needle holder of the first preferred embodiment; therefore, the foregoing description is referred to. The joint 8 in the form of a box joint is complementarily formed on the respective other legs 3a, 3b, as compared to the first embodiment from FIG. 1 to FIG. 4. The first leg 3a is slit in the area of the joint 8, with flat parallel sides (thus forming the through box), and is prepared for receiving the joint portion (through portion) of the second leg 3b which at this point is slim and substantially rectangular. The distal gripping portions 6a, 6b are closed and the opposite locking portions 4a, 4b are in locking engagement with each other in a third stop position. In the third stop position, the gripping force of the gripping areas 6a, 6b is correspondingly higher than in the second stop position.

Figure 6A:
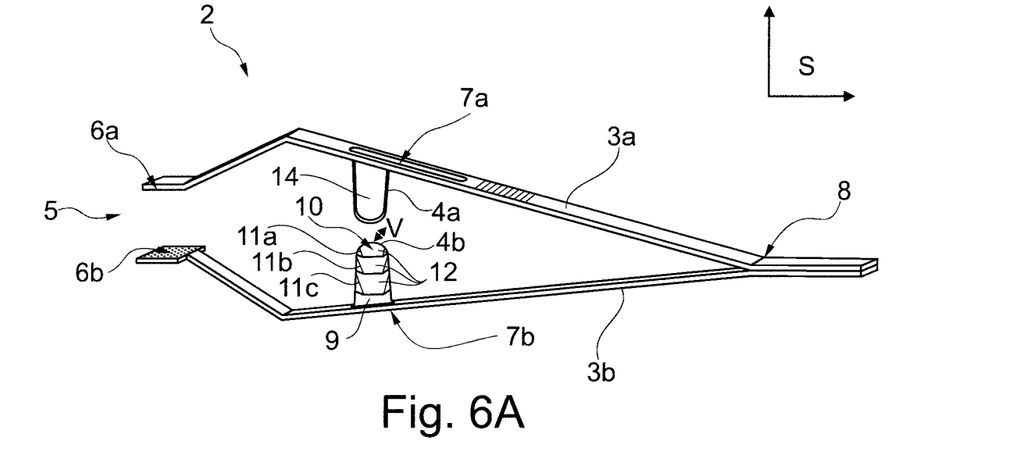
FIG. 6A shows a view of another preferred embodiment of the surgical instrument in the form of forceps with the distal gripping portions being open and the locking portions not being in locking engagement.
Figure 6B:
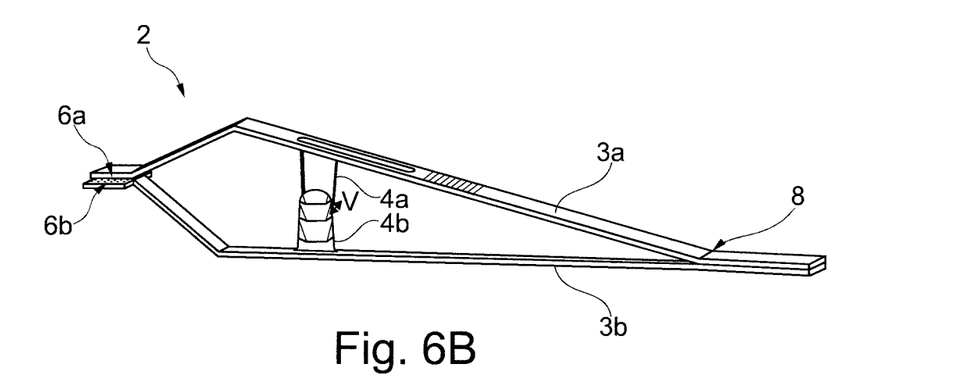
FIG. 6B shows a view of the forceps from FIG. 6A with the distal gripping portions being closed and the locking portions not being in locking engagement.
Figure 6C:
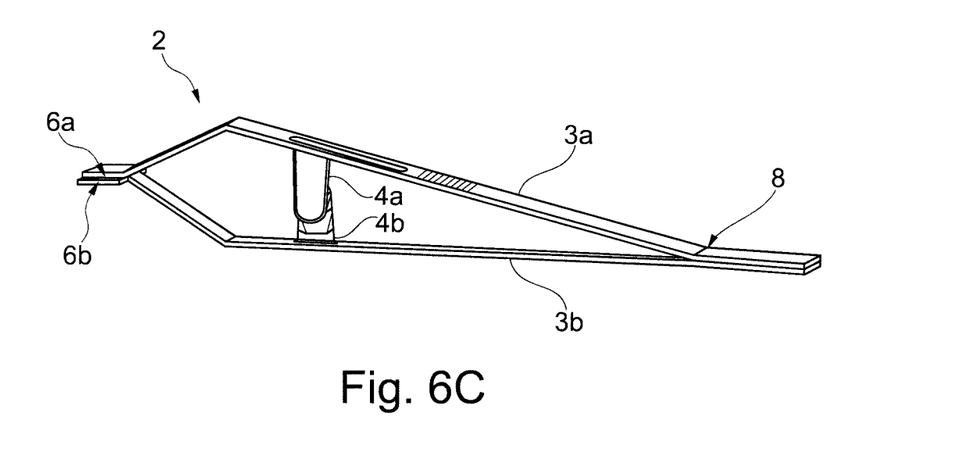
FIG. 6C shows a further view of the forceps from FIGS. 6A and 6B, wherein the distal gripping portions are closed and the opposite locking portions are in locking engagement in a second snap-fit position.

FIGS. 6A to 6C illustrate a medical or surgical instrument according to the invention of a further preferred embodiment which is in the form of forceps 2. FIG. 6A shows the forceps 2 in an opened state, viz. having opened gripping portions 6a and 6b. In contrast to the needle holder 1, in the forceps 2 the actuating areas 7a, 7b are not arranged at the proximal end but merely proximally behind the distal end 5 of the distal clamping portions 6a, 6b. The two (forceps) legs 3a, 3b of the forceps 2 do not cross but are connected to each other at the proximal end via an elastic joint/elastic joint portion 8. The two locking portions 4a, 4b are arranged at the opposing sides of the legs 3a, 3b in the area of the actuating portions 7a, 7b and are formed integrally with the legs 3a, 3b. The actuating portions 7a, 7b are in the form of ergonomic recesses at the legs 3a, 3b which enable both a transverse force and a pressure to be applied so as to move the two legs 3a, 3b against each other in the pivoting plane S and to deflect the two legs 3a, 3b normal to the pivoting plane S against each other and to cancel the offset V.

In the forceps 2 the afore-described procedure of the needle holder 1 is similarly applied again to the locking engagement of the locking portions 4a, 4b and to disengaging the locking. The locking portions 4a, 4b of the forceps are formed identically with the locking portions 4a, 4b of the needle holder 1. The forceps 2 includes inserts made from hard metal in the area of the gripping portions 6a, 6b.

FIG. 6B illustrates the forceps 2 in a closed state in which the locking portions 4a, 4b are not in locking engagement. This state is achieved by the fact that the operating surgeon applies pressure in the pivoting plane S to the two legs 3a, 3b so as to elastically deflect/pivot the two legs 3a, 3b in the pivoting plane S relative to each other. The two locking portions 4a, 4b are laterally passing each other without getting into locking engagement. When the operating surgeon stops applying pressure to the legs 3a, 3b of the forceps 2, the forceps will automatically open again due to the elastic deflection of the legs 3a, 3b relative to each other.

In FIG. 6C, the forceps 2 is shown in a closed and locked state (locking engagement of the locking portions 4a, 4b). Due to the offset V of the legs 3a, 3b against each other, at least one of the gripping portions 6a, 6b, in this case the second gripping portion 6b, has a larger dimension in the direction normal to the pivoting plane S than the first gripping portion 6a. Secure grasping is enabled in locking engagement as well as during opening and closing of the forceps 2 without any locking engagement of the locking portions 4a, 4b.

Figure 7:
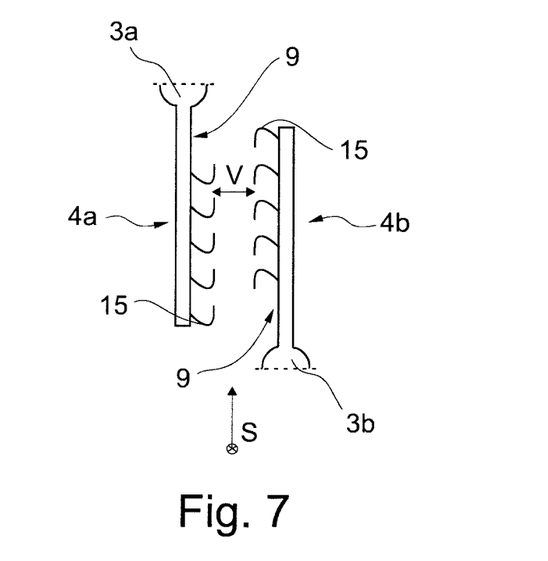
FIG. 7 shows a rear view of a schematic representation of another preferred embodiment of the locking portions of the surgical instrument including a stop structure or, resp., locking engagement side configured with hooks which are formed at the locking portions on sides facing each other.

FIG. 7 schematically shows, in the form of a pictogram, another preferred embodiment of the locking portions 4a, 4b for a medical or surgical instrument 1, 2. The locking portions 4a, 4b include, on their locking engagement side 9 and, resp., locking engagement side, hooks 15 as a stop structure 10 for positive locking engagement. The first locking portion 4a again is arranged complementarily to the second locking portion 4b and the free ends of the hooks 15 point toward the respective leg 3a, 3b. In this embodiment, the locking engagement sides 9 of the locking portions 4a, 4b point toward each other and, resp., are formed on sides of the locking portions 4a, 4b facing each other. The locking portions 4a, 4b include, during (normal) pivoting of the legs 3a, 3b, an offset V which maintains the facing locking engagement sides 9 disengaged. Only when the offset V is cancelled, will the hooks 15 of the two locking portions 4a, 4b get caught and lock the medical or surgical instrument. Instead of designing the locking engagement side 9 with hooks 15, also a design with Velcro fastener (not shown) having two equal or two different Velcro elements/Velcro surfaces (not shown) on the respective locking portions 4a, 4b is imaginable.

Figure 8:
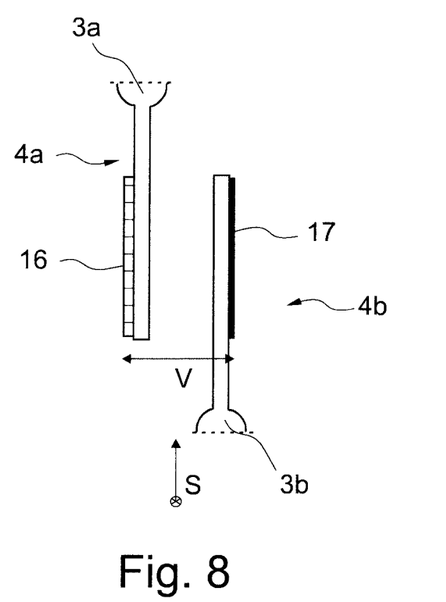
FIG. 8 shows a rear view of a schematic representation of another preferred embodiment of the locking portions of the surgical instrument, with the locking engagement being implemented by means of an adhesive lining which is provided on sides of the locking portions facing away from each other.

FIG. 8 schematically illustrates, in the form of a pictogram, another preferred embodiment of the locking portions 4a, 4b for a medical or surgical instrument 1, 2, comprising an adhesive lining 16 for an adhesive material connection on the side remote from the locking portions 4a, 4b. The adhesive lining 16 is formed merely on the locking portion 4a, whereas the locking portion 4b includes a rough surface or a complementary surface 17 which, when cancelling the offset V and disengaging the two locking portions 4a, 4b, adheres to the adhesive lining 16 and locks the legs 3a, 3b. The adhesive lining 16 and the complementary surface 17 are arranged on sides of the locking portions 4a, 4b remote from each other. Of course, instead of the complementary surface also a second adhesive lining 16 may be provided.

Figure 9:
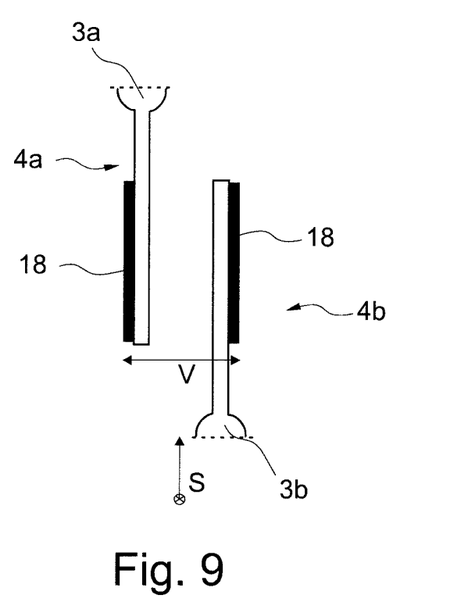
FIG. 9 shows a rear view of a schematic representation of another preferred embodiment of the locking portions of the surgical instrument, with the locking engagement being implemented by means of a friction lining which is provided on sides facing away from each other.

Instead of the adhesive lining 16 and, resp., of the complementary surface 17 of FIG. 8, another embodiment of the locking portions 4a, 4b shown in FIG. 9 for a medical or surgical instrument 1, 2 includes a friction lining 18 for a frictional connection. The friction lining 18 in this embodiment is formed at both locking portions 4a, 4b on sides remote from each other. The friction lining produces high friction in the case of locking engagement of the locking portions 4a, 4b and thus locks the legs 3a, 3b (in a continuously variable manner).

Figure 10:
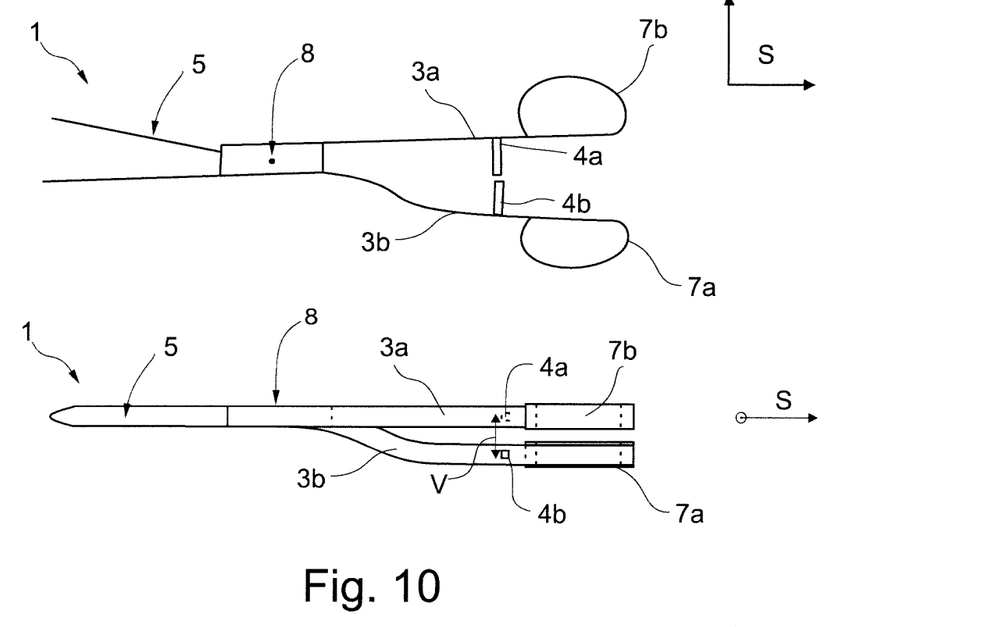
FIG. 10 shows a side view and a top view of a schematic representation of a preferred embodiment of the surgical instrument in the form of a needle holder, with one leg taking an S shape.

FIG. 10 shows a schematic representation of a preferred embodiment of the surgical instrument in the form of a needle holder 1 in a side view and in a view from above/top view. The first leg 3a is located in the pivoting plane S and the second leg 3b takes an S shape relative to the pivoting plane S. Proximally to the joint 8, in the longitudinal direction the second leg 3b thus has an extension with a perpendicular component relative to the pivoting plane S and, in this way, implements the offset V between the locking portions 4a, 4b.

Figure 11:
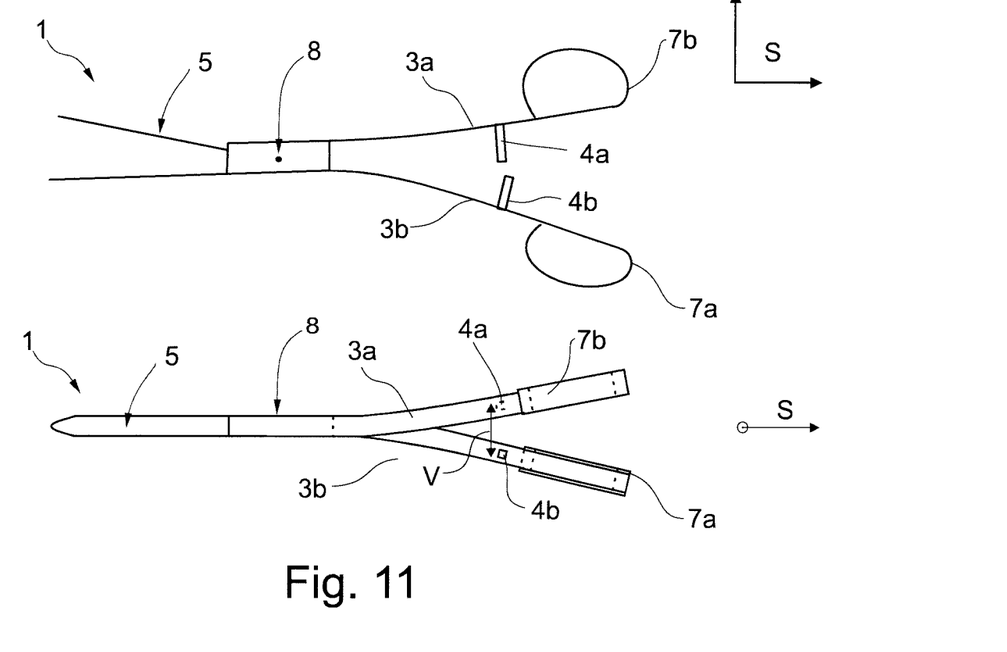
FIG. 11 shows a side view and a top view of a schematic representation of another preferred embodiment of the surgical instrument in the form of a needle holder, with both legs including an opposed bending normal to the pivoting plane.

FIG. 11 illustrates, in a side view and in a top view, a schematic representation of another preferred embodiment of the surgical instrument in the form of a needle holder. The substantial difference from the needle holder of FIG. 10 resides in the implementation of the offset V. In this embodiment, the offset V has been obtained by an opposed bending of the two legs 3a and 3b normal to the pivoting plane S. The legs 3a, 3b extend from the joint 8 in the proximal direction, with the longitudinal axes thereof having an increasing distance from each other normal to the pivoting plane S in the course from distal to proximal and thus producing an offset V of the locking portions 4a, 4b.

Although in the foregoing the present invention has been described by way of embodiments, it is understood that different configurations and modifications may be carried out without leaving the scope of the present invention. In particular, the legs 3a, 3b may take further forms and designs so as to implement the offset V or the offset V is formed by the design of the locking portions 4a, 4b, for example.

The invention claimed is:

1. A medical or surgical instrument comprising at least two legs pivoting relative to each other in a pivoting plane and lockable in at least one pivoting direction and in at least one pivoting position, wherein the at least two legs include locking portions that are rigidly fixed to and non-rotatable relative to the at least two legs, the locking portions adapted to be brought into a locking engagement with each other, wherein the locking portions are offset against each other normal to the pivoting plane such that, when the at least two legs are pivoted in the pivoting plane, the locking portions laterally pass each other without entering into the locking engagement with each other, and the medical or surgical instrument is configured so that the locking engagement of the locking portions is implemented only by applying a transverse force normal to the pivoting plane to at least one of the at least two legs while cancelling the lateral offset.

2. The medical or surgical instrument according to claim 1, wherein the locking engagement is implemented by form-closure and/or frictionally and/or adhesively.

3. The medical or surgical instrument according to claim 1, wherein at least one leg of the at least two legs as a whole or at least a portion thereof is designed to be elastic.

4. The medical or surgical instrument according to claim 1, wherein the locking portions are offset against each other normal to the pivoting plane such that, when the at least two legs are pivoted in the pivoting plane, the locking portions include a gap therebetween so that the locking portions are passing each other without contacting each other.

5. The medical or surgical instrument according to claim 1, wherein the locking portions are arranged at sides of the at least two legs facing each other.

6. The medical or surgical instrument according to claim 1, wherein at each of their distal ends the at least two legs include a respective gripping portion actuatable via actuating portions, wherein a first locking portion of the locking portions is arranged relative to the pivoting plane on a first leg of the at least two legs opposite to a first actuating portion of the actuating portions, and a second locking portion of the locking portions is arranged relative to the pivoting plane on a second leg of the at least two legs opposite to a second actuating portion of the actuating portions.

7. The medical or surgical instrument according to claim 1, wherein the locking engagement is implemented by a form closure and, for this purpose, each of the locking portions has a locking engagement side with a geometric stop structure, wherein the locking engagement sides arranged complementarily on the at least two legs relative to the pivoting plane in the locking engagement in the at least one pivoting direction admit further pivoting of the at least two legs in the pivoting plane and lock the at least two legs in another pivoting direction opposite the at least one pivoting direction.

8. The medical or surgical instrument according to claim 7, wherein the geometric stop structure of the locking portions includes more than two stop planes, wherein during the locking engagement of the locking portions, an increase in a gripping force of the medical or surgical instrument is achieved by increasing a number of stop planes provided in the locking engagement.

9. The medical or surgical instrument according to claim 7, wherein when viewed perpendicularly to the pivoting plane, the locking portions include a smooth side opposite to the locking engagement side and rounded at the edges so as to prevent the locking portions from inadvertently latching when the at least two legs are pivoted in the pivoting plane.

10. The medical or surgical instrument according to claim 1, wherein at least a portion of at least one leg of the at least two legs has an extension in the longitudinal direction, the extension having a perpendicular component relative to the pivoting plane.

11. The medical or surgical instrument according to claim 7, wherein at least the locking engagement side of the locking portions includes wear-resistant material or at least a surface is provided or coated with wear-resistant material.

12. The medical or surgical instrument according to claim 2, wherein the locking engagement is implemented by a stop structure and/or by an adhesive lining and/or by a friction lining.

13. The medical or surgical instrument according to claim 7, wherein, when viewed in the direction normal to the pivoting plane, the locking engagement sides of the locking portions are facing away from each other in a non-locked state.

14. The medical or surgical instrument according to claim 7, wherein, when viewed in the direction normal to the pivoting plane, the locking engagement sides of the locking portions are facing each other in thein a non-locked state.

15. The medical or surgical instrument according to claim 5, wherein the locking portions are integrally formed in one piece of material on the at least two legs.

16. The medical or surgical instrument according to claim 7, wherein each locking engagement side with the geometric stop structure is in the form of a toothing including at least one tooth.

17. The medical or surgical instrument according to claim 10, wherein the at least two legs include an opposed bending to a proximal side normal to the pivoting plane away from each other.

18. The medical or surgical instrument according to claim 13, wherein the locking engagement sides of the locking portions are formed substantially in parallel to each other.

19. A medical or surgical instrument comprising at least two legs pivoting relative to each other in a pivoting plane and lockable in at least one pivoting direction and in at least one pivoting position, wherein the at least two legs include locking portions adapted to be brought into a locking engagement with each other, wherein the locking portions are offset against each other normal to the pivoting plane such that, when the at least two legs are pivoted in the pivoting plane, the locking portions laterally pass each other without entering into the locking engagement with each other, the medical or surgical instrument is configured so that the locking engagement of the locking portions is implemented only by applying a transverse force normal to the pivoting plane to at least one of the at least two legs while cancelling the lateral offset, wherein at least a portion of at least one leg of the at least two legs in the longitudinal direction has an extension with a perpendicular component relative to the pivoting plane, and wherein the at least two legs include an opposed bending to a proximal side normal to the pivoting plane away from each other.

20. The medical or surgical instrument according to claim 19, wherein the at least one leg of the at least two legs as a whole or at least a portion thereof is designed to be elastic.

* * * * *